United States Patent [19]
Weinstein et al.

[11] Patent Number: 5,312,479
[45] Date of Patent: May 17, 1994

[54] INVERTED DOME ARTERIAL FILTER

[75] Inventors: Martin J. Weinstein, Salisbury, Mass.; Alfred P. Intoccia, Nashua, N.H.

[73] Assignee: C. R. Bard, Inc., Murray Hill, N.J.

[21] Appl. No.: 52,787

[22] Filed: Apr. 23, 1993

[51] Int. Cl.$^5$ .............................................. B01D 19/00
[52] U.S. Cl. .......................................... 96/178; 96/179; 96/209; 96/212; 210/188; 210/304; 210/436; 210/472
[58] Field of Search .............. 55/337; 96/6, 177, 179, 96/208, 209, 212, 178; 210/188, 304, 436, 448, 492, 493.2, 494.1

[56] References Cited
U.S. PATENT DOCUMENTS

| | | |
|---|---|---|
| Re. 32,711 | 1/1988 | Dickens et al. . |
| 3,701,433 | 10/1972 | Krakauer et al. . |
| 3,795,088 | 3/1974 | Esmond . |
| 3,827,562 | 8/1974 | Esmond . |
| 3,849,071 | 11/1974 | Kayser . |
| 3,939,078 | 2/1976 | Servas et al. . |
| 4,038,194 | 7/1977 | Luceyk et al. . |
| 4,344,777 | 8/1982 | Siposs . |
| 4,490,254 | 12/1984 | Gordon et al. . |
| 4,964,984 | 10/1990 | Reeder et al. ................. 210/472 X |

*Primary Examiner*—Charles Hart
*Attorney, Agent, or Firm*—Spensley Horn Jubas & Lubitz

[57] ABSTRACT

An arterial filter includes a filter housing provided with a uniquely shaped housing cover. The housing cover is in the shape of a toroid which forms a coil-like tunnel which is enlarged midway about the circumference of the housing cover. The highest point of the toroidal channel is at the periphery of the housing cover, approximately 180° from the inlet valve. A gas vent is located at this highest point on the top of the toroid-shaped housing cover. At the center of the housing cover is an indentation which is provided to both retain a cylindrical filter element inside the filter housing, as well as allow visibility directly through the central axis of the arterial filter to verify proper operation of the filtration process. As inlet blood circulates through the toroidal tube forming the filter housing cover, gaseous matter is allowed to buoyantly escape out of the gas vent located at the top of the raised section of the toroidal channel. The remaining debubbled fluid seeps down into a reservoir formed between the cylindrical filter housing and the outer perimeter of the filter element contained therein. The filter element draws the fluid toward the center of the filter housing, as it simultaneously filters out undesired particulate and gaseous matter. The filtered product then passes into the hollow central area of the filter element and exits through an outlet vent located at the bottom of the filter housing.

24 Claims, 3 Drawing Sheets

INVERTED DOME ARTERIAL FILTER

BACKGROUND OF THE INVENTION

1. Field of the Invention

The present invention relates to filters which are used, for example, in extra corporeal circuits for removal of particulate and gaseous matter. Particularly, embodiments of the present invention relate to a disposable arterial blood filter for use in extra corporeal blood flow circuits, such as in a bypass circuit, for filtering out solid or gaseous emboli.

2. Description of Related Art

Disposable arterial filters have been used for the treatment and filtration of blood for various applications such as cardiopulmonary bypass techniques, blood transfusions, dialysis treatments, etc. The arterial filter is provided to trap and remove gaseous and particulate matter from oxygenated blood. Typically, the arterial filter is one of the components in an extracorporeal blood flow circuit in which blood flows from a patient's body, through a cardiotomy reservoir, an oxygenator, and finally into the arterial filter before it is returned to the patient. Thus, the arterial filter may be the last component of the extracorporeal blood flow circuit through which blood traverses before it returns to the patient.

Certain conventional blood filters include a hollow tubular housing containing a concentric cylindrical filter element and a perforated tubular core disposed inside the cylindrical filter element. U.S. Pat. No. Re. 32,711 to Dickens et al. discloses such an arterial filter design. The perforated core is provided to support, or brace, the filter material within the tubular housing and is thus designed to reduce the possibility of collapse at high flow rates.

This type of conventional structure typically utilizes a pleated filter element contained within a tubular housing unit having a dome-shaped cover. A perforated plastic core is concentrically disposed in the center of the cylindrical filter material to support, or hold up, the filter element within the housing. A conical cap forming an upwardly directed peak separates the end of the cylindrical filter material from a generally flat housing cover. A gas vent is centrally disposed at the apex of the dome-shaped housing cover. The conical cap causes inlet blood to swirl and create a vortex between the conical cap and the housing cover. This vortex action purportedly drives gaseous matter toward the center of the housing cover to escape through the gas vent located at the center of the cover.

In such designs, however, because the gas vent is located at the center of the housing cover (displaced from the outer periphery portion of the cover), and because the filter cap inside the housing forms a peak at its center, there is limited visibility of the filtration process from inlet to outlet. Thus, confirmation of the filter properly receiving and passing blood and of proper debubbling and uniform filtration of the liquid may be difficult if not impossible.

In addition, because such conventional blood filters typically employ a coarse outer support screen, such as netting or other large-pored materials, bubbles in the liquid often become undesirably entrapped within the gaps in the outer filter material. Consequently, such conventional blood filters require rigorous and prolonged agitation of the fluid inside the filter housing to dislodge any bubbles trapped during both the priming process and actual filtration. As a result, to minimize damage to the filter media during the prolonged agitation, the perforated core is provided to support the filter element as it is impacted by the agitated fluid flowing within the housing.

Moreover, although such conventional arterial filters provide a finer inner filter layer adjacent the coarse, large-pored external filter material, the desired orderly venting of gas often cannot be attained due to the presence of gaseous matter which may already have collected in the coarse outer filter layer. As a consequence, further agitation may be necessary to loosen and prevent any gaseous emboli from passing through the filter layers.

SUMMARY OF THE DISCLOSURE

Accordingly, it is an object of a preferred embodiment of the present invention to provide an improved arterial filter having simple construction, yet providing for precise and efficient filtering of gaseous and particulate debris from fluids, such as oxygenated blood.

An arterial blood filter according to an embodiment of the invention is particularly suitable for filtering gaseous and particulate matter from oxygenated blood which has exited a patient's body, and has passed through an oxygenator before reaching the arterial filter. The illustrated embodiment of the arterial filter is relatively simple in construction and easy to use. In addition, proper operation may be readily confirmed during priming and actual use.

The filter illustrated in FIGS. 1 and 2 includes a transparent cylindrical housing having a closed bottom end and an open top end which is covered by a housing cover. Contained within the housing is a porous cylindrical filter element, concentrically located with respect to the central longitudinal axis of the housing. A blood outlet port is provided at the bottom of the housing, adjacent the hollow central area of the cylindrical filter.

The housing is enclosed by a transparent doughnut or toroid-shaped housing cover having an indentation in its center. The indentation is coupled to the top of the cylindrical filter element to support and hold the filter element in place within the filter housing, between the bottom of the housing and the indentation in the cover. The indentation, therefore, obviates the need for a central core for supporting the filter element, as required in the above discussed conventional structure.

The doughnut-like curvature provides a toroidal channel or tunnel through which entering fluid is guided. The toroidal housing cover forms a coil-like tunnel which is enlarged approximately 180° from a blood inlet port provided at one end of the toroid-shaped housing cover. This enlarged area defines the highest point on the housing cover. A gas vent is located at the highest point on the toroidal tunnel, at the periphery of the housing cover.

Fluid enters the tangential blood inlet and circulates through the toroidal channel. As the fluid flows about the toroidal channel, gaseous matter is drawn upward by buoyant forces and is allowed to escape through the peripheral gas vent, while the fluid seeps down into a reservoir formed between the inner wall of the housing cover and the outer perimeter of the cylindrical filter element. The gentle swirling action of the entering fluid through the toroidal channel is sufficient to cause the fluid to flow completely about the housing cover and seep down around the sides of the filter element. The fluid flows through the filter element into the hollow central cylindrical cavity of the cylindrical filter element, where the filtered fluid is then allowed to exit through the outlet prot provided at the bottom of the housing. The filtered fluid is then directed into the patient's body.

By definition, the toroid-shaped housing cover is provided with an indentation in the center of the toroid. The circular indentation covers the top of the cylindrical filter element and securely holds the filter element vertically within the cylindrical housing. The top of the filter element is rigidly affixed to the indentation by a potting material between the indentation and the top of the filter element. The filter element is similarly affixed to the bottom of the filter housing. This arrangement provides a rigid and secure support structure to prevent collapse of the filter element as fluid flows through the filter housing. Accordingly, the support provided by the toroid indentation and the bottom of the filter housing obviates the need for further bracing components such as a central support rod or core.

Furthermore, the generally flat indentation has a circumference slightly larger than the inner circumference of the cylindrical filter material so that an operator or perfusionist may clearly see through the hollow area in the center of the cylindrical filter element, down to the outlet port at the bottom of the housing. Thus, not only is the filter material clearly visible through the transparent cylindrical housing, but the flow of fluid through the filter material into the inner central cavity within the filter element is also visible through the flat indentation in the center of the toroidal housing cover.

DETAILED DESCRIPTION OF THE INVENTION

The following description is of the best presently contemplated mode of carrying out the invention. In the accompanying drawings, like numerals designate like parts in the several figures. This description is made for the purpose of illustrating the general principals of embodiments of the invention and should not be taken in a limiting sense. The scope of the invention is best determined by reference to the accompanying claims.

Figure 1:
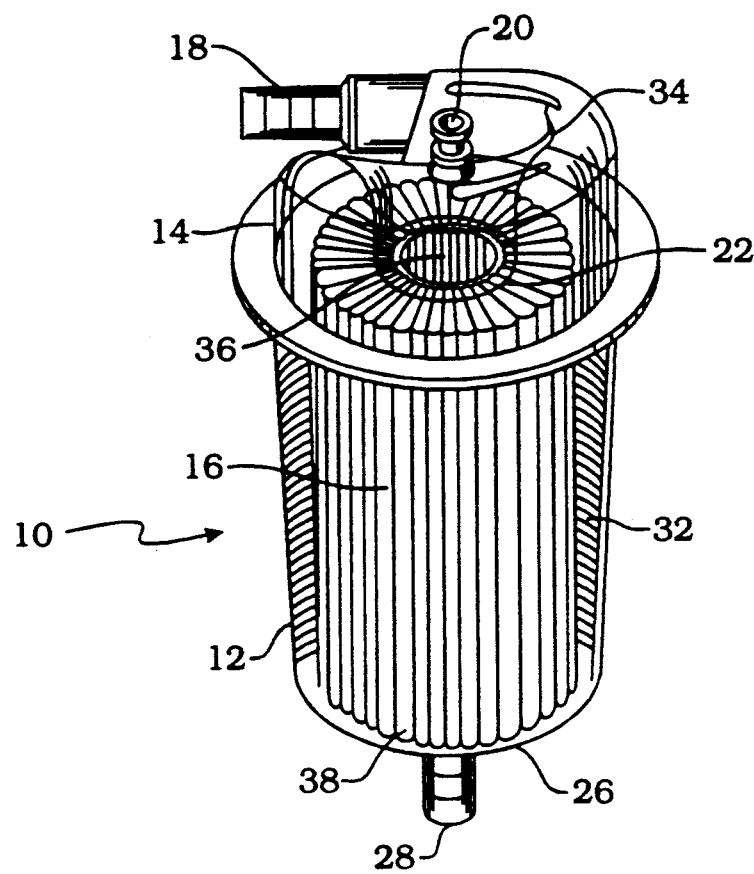
FIG. 1 is a perspective view of an arterial blood filter according to an embodiment of the invention.

FIG. 1 shows a perspective view of a disposable arterial blood filter 10 according to an embodiment of the invention. As discussed in greater detail below, embodiments of the present invention are used to trap and remove gaseous and particulate matter from oxygenated blood. In a preferred embodiment, the arterial filter is incorporated into an extracorporeal blood flow circuit, in which oxygenated blood passes through the filter before it is supplied to a patient. The blood flow circuit may include, for example, a blood oxygenator upstream from the arterial filter.

The illustrated embodiment is particularly suitable for use as an arterial filter for filtering blood and blood products. As will be apparent from the discussion below, certain aspects of embodiments of the invention provide significant advantages in the filtering of blood or blood products. It will be recognized, however, that further embodiments of the invention may be used for a variety of different filtration purposes for filtering other fluids such as water or oil.

A first embodiment of the invention is shown in FIG. 1, in which the arterial filter comprises a transparent cylindrical filter housing 12, a toroid-shaped housing cover 14, a cylindrical filter 16 concentric with the central axis of the filter housing, a tangential inlet valve 18 located at the side of the housing cover 14, a gas vent 20 positioned at the top of the housing cover, and an outlet port formed in the center of the bottom 26 of the housing 12.

As described in detail below, various features of the illustrated embodiment provide significant advantages over the above-discussed prior art. For example, the toroidal housing cover 14 defines a central indentation, and the housing cover 14 and the cylindrical housing 12 are transparent. With these features, an operator or perfusionist can readily observe fluid flowing into the arterial filter and can also view (through the central indentation) the center cavity of the filter element 16 contained within the housing 12.

While shapes other than a toroid may be used for further embodiments, in a preferred embodiment, the housing cover 14 has a toroidal configuration. The toroidal configuration provides a smooth, curved flow path of maximum radius to minimize or reduce aggressive agitation of the fluid during its flow. Due to the central indentation 22 defined by the toroid-shaped housing cover 14, the curved fluid flow path is radially spaced from the central axis of the housing 12. This allows the radius of curvature of the fluid flow path (and, thus, the length of the path) to be maximized, while containing the path within the housing cover. Maximizing the length of the fluid flow path tends to maximize the time period in which a given volume of fluid flows through the length of the path (for a given flow velocity) and, therefore, maximizes the amount of time in which gas bubbles may be drawn from the fluid.

The curved fluid flow path also tends to gently guide the fluid around the upper periphery of the underlying filter element 16, such that the fluid can flow downward around substantially the entire outer peripheral surface of the filter element and then pass through the filter element from all radial directions with minimal agitation and turbulence. Consequently, the undesired generation of air bubbles is also minimized. This allows the entire filter element to be efficiently used and maximizes the rate at which a given volume of fluid may be passed through the filter element.

Figure 2:
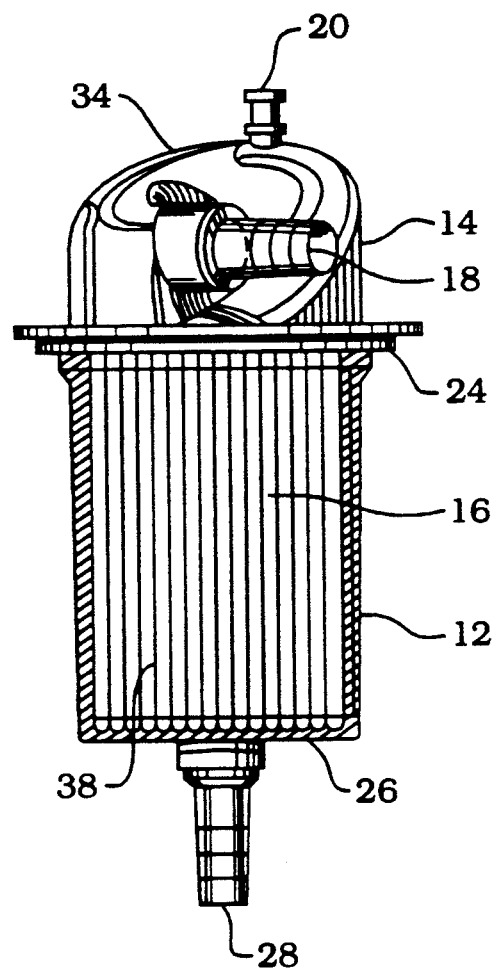
FIG. 2 is a side view of the filter shown in FIG. 1.
Figure 4:
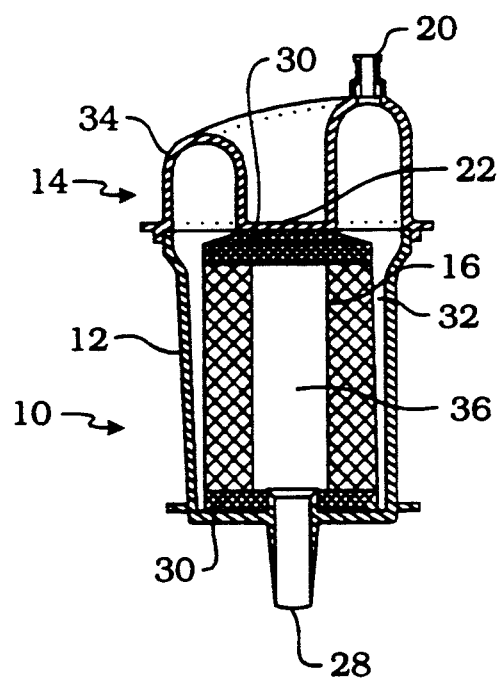
FIG. 4 is a cross-sectional side view of the filter of FIG. 1.

Referring to FIGS. 1, 2 and 4, the toroid-shaped housing cover 14 is configured to guide fluid (not shown) in a curved path over the filter housing 12 as it enters the arterial filter 10. In a preferred embodiment, the cylindrical housing 12 is permanently joined to the housing cover 14 by hot-melt bonding or other adhesive means. It will be readily recognized, however, that the housing cover 14 may also be affixed to the housing 12 by various other means such as snap-fit edges, a screw-on type closure, or other interlocking structure.

Figure 3:
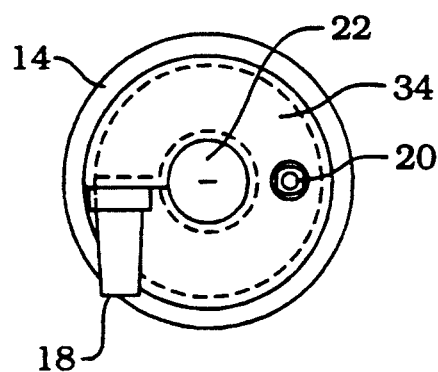
FIG. 3 is a top view of the filter of FIG. 1.

The housing cover 14 has a toroidal, doughnut-like shape. The height of the toroid 34 forming the housing cover 14 rises as it curves about the perimeter of the housing cover 14. As shown in FIGS. 2-4, the highest point of the housing cover 14 is located midway around the toroid curvature, approximately 180° from the tangential inlet port 18.

A gas vent cap 20 is located at the perimeter of the housing cover 14, at the highest point on the cover, opposite the inlet port 18. The side view of the arterial filter 10 depicted in FIGS. 2 and 4 shows a preferred arrangement of the gas vent 20 disposed on the highest point on the toroidal channel, at the periphery of the housing cover 14. In the preferred embodiment, the gas vent 20 is a one-way valve, such as a female Luer cap, which allows gas to escape but does not permit air or particulate matter to enter.

Because the gas vent 20 is located at the highest point on the toroid-shaped housing cover 14, approximately 180° opposite the tangential inlet port 18, as the inlet liquid is caused to swirl through the toroidal channel 34, gaseous matter rises, by buoyant forces, to the highest point of the filter and exits through the gas vent 20. Yet, due to the swirling action, the inlet fluid still retains sufficient momentum to flow through the remaining half of the downwardly sloping toroidal channel to flow steadily and evenly around the perimeter of the toroidal channel of the housing cover 14, before seeping downward into the housing reservoir 32. This feature is discussed in more detail below.

FIG. 4 also illustrates an indentation 22 formed in the center of the toroid-shaped housing cover 14. As discussed in more detail below the indentation 22 serves to stabilize and support the filter element 16 as well as provide clear visibility of the filtered fluid after it passes through the filter element 16 into the central cavity 36 of the filter element 16. The configuration of the housing cover 12 and the indentation 22 comprises an inverted dome cap which, in preferred embodiments, defines a toroidal-shaped fluid flow path.

The cylindrical filter element 16 is contained inside a filter element chamber defined by the cylindrical housing 12. The filter element 16 rests on the housing bottom 26 and extends approximately to the housing lip 24, where the filter housing 12 meets the housing cover 14. The filter element 16 is concentric with the central longitudinal axis of the housing such that the central cavity of the cylindrical filter element 16 encircles the fluid outlet port 28 located at the center of the bottom 26 of the housing 12.

In contrast with conventional blood filters discussed above, there is no central stabilizing core or bar extending down the central axis of the cylindrical filter 16, as indicated in FIGS. 1 and 4. In the illustrated embodiment, such a stabilizing support core is not needed to prevent collapse of the filter element 16 because, as will be discussed below, the cylindrical filter element 16 is firmly maintained in its vertical, concentric position by the central indentation defined by the toroid-shaped housing cover 14.

In the preferred embodiment, the filter element 16 is formed of multiple layers of filter material. The filter material 16 includes a sheet of webbed netting material layered adjacent a thin, finely-pored filtered fabric. The webbed, netting layer comprises the inner layer of the pleated sheet. The smooth, finely-pored filter fabric comprises the outer filter screen. The smooth finish of the outer filter screen obviates the need for harsh, rigorous and prolonged agitation which would otherwise be required to dislodge bubbles trapped in a large-pored material, such as the netting screen, during a priming process or during actual filtration use.

It should be noted that priming may be necessary to wet the filter 10 before the desired fluid to be filtered, such as blood, is circulated therethrough. Priming is typically performed with saline solution. The saline solution is directed into the filter inlet port 10, swirls through the housing cover, and seeps down into the housing reservoir 28. The priming solution is then drawn into the filter element 16 to dampen, and thus prime, the filter 10.

In addition, priming is performed to remove undesirable air bubbles contained inside the housing 12 of the filter before filtration begins. The saline solution is allowed to pass through the filter material to "debubble" the housing chamber 12 before the fluid to be filtered is run through the filter housing. Thus, after the saline solution is passed through the filter element 16, air bubbles are separated from the solution by the filter screen. These bubbles then rise buoyantly toward the housing cover 14 and escape through the gas vent 20 at the periphery of the cover 14.

Thus, it can be seen that during actual filtration, not only does the smooth outer filter screen inhibit bubbles from lodging in the filter element pores, but the filter screen further operates to provide basic filtering functions for filtering the undesirable particulate and residual gaseous matter from the fluid during actual use.

Preferably, the double layer filter sheet is pleated and arranged in a cylindrical configuration. This pleated filter structure is depicted in FIGS. 1 and 2. The pleats 38 in the filter material 16 provide an increased filter surface area and allow uniform filtration through both the smooth outer filter fabric layer and the coarse inner filter layer. Thus, the flow of filtered fluid is evenly spread throughout the surface area of the filter element 16.

As described above, the indentation 22 in the center of the housing cover defines the inverted dome cap of the illustrated embodiment of the present invention. One of the noted advantages of this indentation 22 is that it functions to maintain the filter element 16 in place within the housing 12. Another advantage provided by the indentation 22 and the transparency characteristic of the housing cover 14 is the ability to allow clear visibility into the central cavity 36 of the filter element 16 so that the operator or perfusionist can visually observe the transfer of filtered fluid through the filter element 16. Thus, proper and uniform filtration can be readily confirmed by visual inspection.

FIG. 1 illustrates an embodiment of the invention in which the inverted dome indentation 22 in the housing cover 14 is adjacent the open end of the filter element 16. Preferably, the outer circumference of the indentation is larger than the inner circumference of the pleated cylindrical filter element 16, so that the indentation 22 is positioned over the end of the filter element 16 and the hollow central area 36 of the filter element 16 is completely enclosed. This enclosure of the central cavity 36 in the cylindrical filter element 16 between the indentation 22 in the housing cover 14 and the bottom 26 of the filter housing 12 is shown in FIG. 4.

Referring to FIGS. 1 and 4, the inverted dome cap is directly coupled to the top of the filter via the indentation 22 and an intermediate adhesive product. A similar adhesive may be used to coupled the bottom end of the filter element 16 to the housing bottom 26. Preferably, the adhesive is a hot-melt bonding adhesive which forms a transparent urethane-like potting 30 covering the entire upper surface of the filter element 16, as shown in FIG. 4. As discussed in greater detail below, the potting structure 30 protects and encases the ends of the filter element 16, and also promotes smooth fluid flow over the top of the cylindrical filter element 16.

Thus, the pleated cylindrical filter element 16 is supported and firmly retained in place by adhering the ends of the filter element 16 to the indentation 22 and the housing bottom 26. This adhesive support arrangement prevents shifting or collapse of the filter element 16 during use as fluid impinges upon the filter material. Consequently, unlike certain conventional arterial filters which require a central support shaft or core for supporting a filter element, the upper and lower potting configuration 30 of the illustrated embodiment provides secure retention of the pleated cylindrical filter media, obviating the need for an additional support structure.

As shown in FIG. 4, the bottom of the hollow central cavity 36 of the cylindrical filter element 16 is not completely filled in with the potting 30, but is left unobstructed to enable filtered fluid to exit the central outlet port 28 at the bottom 26 of the housing 12. As will be described below, the complete enclosure of the cylindrical filter element 16 allows efficient and precise filtering of fluid that impinges any available surface area on the filter element 16.

The toroid-shaped housing cover 14 and its integral indentation 22 are preferably made of a clear polycarbonate material to provide increased visibility from the fluid inlet port to the outlet port. Preferably, the urethane-like potting material 30 at the top and bottom of the filter element 16 is also transparent to enhance the visibility of the central cavity 36 within the filter element 16 during the filtration process.

These features allow an operator or perfusionist to visually monitor the debubbling process and filtration results during priming and actual use. That is, the toroidal fluid flow path in the housing cover 12 is visible through the outer peripheral surface of the cover 14, and the filter element central cavity 36 and the outlet port 28 are visible through the indentation 22. As a result, proper performance throughout the filter can be visually verified. Moreover, because the need for an additional filter element support structure (e.g., a central core or shaft) is obviated, as described above, the complexity and cost of manufacture of the arterial filter and its components are significantly reduced.

In operation, the toroid-shaped housing cover 14 acts as an air separation chamber. When a fluid, e.g., a priming fluid or blood, enters the tangential inlet port 18 via a tube or other fitting, it flows tangential to the wall of the toroidal channel 34 and through the curved path defined by the channel. The flowing motion creates a gentle swirling action which causes air and other gaseous matter to be separated from the fluid inside the toroidal channel 34. Consequently, in accordance with the principles of buoyancy, the gaseous matter rises and escapes through the peripheral vent cap 20 which is located on the highest point about the toroidal channel 34.

As the gaseous matter is separated from the fluid, the swirling debubbled fluid seeps downward from the periphery of the toroidal tunnel 34, over the potting 30 and the filter element 16, and into the reservoir 32 formed between the inner wall of the housing 12 and the outer perimeter of the filter material 16, as shown in FIG. 4. As the fluid fills the housing reservoir 32, it uniformly impinges upon the filter element 16 and is drawn into the layers of filter material. The fluid passes through the filter element 16 where further undesirable gaseous and particulate matter are separated and filtered out by the smooth outer filter screen and the coarse inner screen. The resultant filtered fluid collected within the central cavity of the filter element 16 is then permitted to exit the arterial filter 10 through the outlet port 28 centrally located at the bottom 26 of the housing 12.

As discussed above, it is preferred that the housing 12 and the housing cover 14 be formed of a transparent polycarbonate material to allow the operator to visually monitor both the debubbling during the priming process as well as the actual operation of the blood filtering process. In addition, preferably the material used in the housing cover 14 as well as the housing 12 is of a particular tint, e.g., light blue, to provide optimum visual contrast, whether the entering fluid is clear saline or darkly pigmented blood.

It will be recognized that while terms such as top and bottom have been used with regard to the illustrated embodiments, such terminology is relative to the actual position and configuration of the illustrated arterial blood filter with respect to a complete extracorporeal perfusion circuit. For example, the horizontal and vertical placement of the arterial filter may vary depending upon the position of the patient as well as upon the positions of the other components of the extracorporeal circuit.

In addition, it will be recognized that while the illustrated embodiment employs flexible layers of filter material, a variety of filter fabrics or other filter structures may be employed, wherein the filter element is maintained between the indentation 22 in the housing cover 14 and the bottom 26 of the filter housing 12.

Furthermore, it is also contemplated that the toroidal configuration of the housing cover may be modified such that the height of the toroid structure is uniform throughout its curvature. For example, the height of the inlet port may be equal to the height of the location on the toroidal channel where the gas vent is placed. Any gaseous matter is still permitted to escape through the gas vent, while the fluid swirling through the toroidal channel seeps downward into the filter housing reservoir 32.

The presently disclosed embodiments are to be considered in all respects as illustrative and not restrictive. The scope of the invention should only be limited by the appended claims, rather than the foregoing description, and all changes which come within the meaning and range of equivalency of the claims are, therefore, intended to be embraced therein.

We claim:

1. A filter for filtering fluids, comprising:
    a housing defining a toroidal channel, a central indentation, and a filter element chamber;
    a fluid inlet in fluid flow communication with the toroidal channel;
    a gas outlet aperture in gas flow communication with the toroidal channel;
    a filter element supported within the filter element chamber by the central indentation of the housing; and
    a fluid outlet in fluid flow communication with the filter element chamber.

2. The filter of claim 1, wherein the toroidal channel and the central indentation are integrally formed in the housing.

3. The filter of claim 1, wherein the height of the toroidal channel rises from the location of the fluid inlet, around the periphery of the housing to a highest point located approximately 180° opposite the fluid inlet.

4. The filter of claim 3, wherein the gas outlet is located at the highest point on the toroidal channel.

5. The filter of claim 1, wherein the housing, the central indentation and the toroidal channel are transparent.

6. The filter of claim 1, wherein the filter element is affixed to the central indentation and the filter element chamber by a transparent potting material.

7. The filter of claim 1, wherein the filter element comprises
   a layer of fine, porous filter material, and
   a layer of a highly porous material, wherein the layer of fine, porous filter material is layered adjacent the highly porous material to form a filter sheet, the layered sheet being pleated into a generally cylindrical configuration.

8. A filter for filtering fluids, comprising:
   a housing defining a filter element chamber;
   a cover having a central indentation and a fluid flow channel curved around the central indentation;
   a fluid inlet in communication with the fluid flow channel;
   a gas outlet aperture in communication with the fluid flow channel;
   a filter element supported within the filter element chamber by the central indentation of the housing; and
   a fluid outlet in communication with the filter element chamber.

9. The filter of claim 8, wherein the fluid flow channel is in the shape of a toroid.

10. A filter for filtering fluids, comprising:
    a housing defining a toroidal channel, a central indentation, and a filter element chamber, wherein the toroidal channel, central indentation and filter element chamber are transparent to provide visibility into the housing;
    a fluid inlet in fluid flow communication with the toroidal channel;
    a gas outlet aperture in gas flow communication with the toroidal channel;
    a filter element contained within the filter element chamber, the filter element defining a central cavity, and having a top end adjacent the central indentation and a bottom end; and
    a fluid outlet in fluid flow communication with the filter element chamber, wherein the transparent central indentation provides for visibility from the fluid inlet to the fluid outlet, through the central cavity of the filter element.

11. The filter of claim 10, wherein the fluid inlet is integrally formed along the perimeter of the toroidal channel.

12. The filter of claim 10, wherein the height of the toroidal channel rises from the location of the fluid inlet, around the periphery of the housing cover to a highest point located approximately 180° opposite fluid inlet.

13. The filter of claim 12, wherein the gas outlet is located at the highest point on the toroidal channel.

14. The filter of claim 10, wherein the filter element is firmly supported in the filter element chamber by the central indentation coupled to the top end of the filter element.

15. The filter of claim 14, wherein the top end of the filter element is affixed to the central indentation and the bottom end of the filter element is affixed to the filter element chamber by a potting material.

16. A filter for filtering fluids containing non-fluid matter, comprising:
    a housing defining a filter chamber;
    a cover for enclosing the housing, the cover having a central indentation and toroidal channel curved around the indentation;
    a fluid inlet in fluid flow communication with the toroidal channel through which the fluid to be filtered enter the filter;
    a gas outlet in gas flow communication with the toroidal channel, for allowing non-fluid matter to escape from the housing cover; and
    filter means for filtering the fluid, the filter means being supported within the filter chamber by the indentation in the housing cover; and
    a fluid outlet in fluid flow communication with the filter chamber such that after the inlet fluid passes through the filter means, the fluid exits the filter chamber through the fluid outlet.

17. The filter of claim 16, wherein the fluid inlet is integrally formed along the perimeter of the toroidal channel.

18. The filter of claim 16, wherein the height of the toroidal channel rises from the location of the fluid inlet, around the periphery of the housing cover to a highest point located approximately 180° opposite the fluid inlet.

19. The filter of claim 18, wherein the gas outlet is located at the highest point on the toroidal channel.

20. The filter of claim 16, wherein the filter means defines a hollow central cavity which is concentric with the housing filter chamber such that the cavity encircles the fluid outlet.

21. The filter of claim 16, wherein the housing, the cover, including the central indentation and the toroidal channel are transparent to allow visibility of the flow of the fluid from the fluid inlet to the fluid outlet.

22. The filter of claim 16, wherein the filter means is affixed to the indentation by a transparent potting material.

23. The filter of claim 16, wherein the filter means is affixed to the filter chamber by a potting material.

24. The filter of claim 16, wherein the filter means comprises
    a layer of fine, porous filter material, and
    a layer of a highly porous material, wherein the layer of fine, porous filter material is layered adjacent the highly porous material to form a filter sheet, the layered sheet being pleated into a generally cylindrical configuration.

* * * * *